US012377242B2

(12) United States Patent
Besselink

(10) Patent No.: US 12,377,242 B2
(45) Date of Patent: Aug. 5, 2025

(54) TUBING FOR MANUFACTURING EXPANDABLE DEVICES

(71) Applicant: Petrus A. Besselink, Enschede (NL)

(72) Inventor: Petrus A. Besselink, Enschede (NL)

(73) Assignee: Memory Metal Holland BV, Enschede (NL)

( * ) Notice: Subject to any disclaimer, the term of this patent is extended or adjusted under 35 U.S.C. 154(b) by 1202 days.

(21) Appl. No.: 17/269,381

(22) PCT Filed: Aug. 19, 2019

(86) PCT No.: PCT/IB2019/000924
§ 371 (c)(1),
(2) Date: Feb. 18, 2021

(87) PCT Pub. No.: WO2020/039253
PCT Pub. Date: Feb. 27, 2020

(65) Prior Publication Data
US 2021/0213242 A1 Jul. 15, 2021

Related U.S. Application Data

(60) Provisional application No. 62/719,736, filed on Aug. 20, 2018.

(51) Int. Cl.
*A61M 25/00* (2006.01)
(52) U.S. Cl.
CPC . *A61M 25/0013* (2013.01); *A61M 2205/0266* (2013.01)

(58) Field of Classification Search
CPC ...... A61M 25/0013; A61M 2205/0266; A61M 25/00; A61F 2/04; A61B 17/083;
(Continued)

(56) References Cited

U.S. PATENT DOCUMENTS 5,885,258 A  3/1999 Sachdeva et al.
6,428,634 B1  8/2002 Besselink et al.
(Continued)

FOREIGN PATENT DOCUMENTS

EP    3031409 A2    6/2016

OTHER PUBLICATIONS

International Search Report and Written Opinion dated Feb. 25, 2020 in related International Application No. PCT/IB2019/000924.

*Primary Examiner* — Jerrah Edwards
*Assistant Examiner* — Jose H. Trevino, III
(74) *Attorney, Agent, or Firm* — Thomas E. Lees, LLC

(57) ABSTRACT

An intra-corporal medical device, a medical device and a method of making an intra-corporal medical device. In one form, the device is formed from one or more tubes with a non-axisymmetric cross-sectional profile such that tines formed in a relatively planar surface of such a device exhibit the ability to accept larger deformations that will have improved mechanical properties, including a lower tendency to buckle under bending forces. In one form, the tube or tubes are made from shape memory materials such as Nitinol that can be expanded or bent in various directions in order to take advantage of shape memory effect, linear and non-linear pseudoelasticity and strain hardened cold work.

23 Claims, 4 Drawing Sheets

(58) Field of Classification Search
CPC .............. A61B 17/122; A61B 17/0401; A61B 17/0487; A61B 2017/00867; A61B 2017/0419; A61B 2017/0427; A61B 2017/0464; A61B 2017/1139
See application file for complete search history.

(56) References Cited

U.S. PATENT DOCUMENTS

| | | | |
|---|---|---|---|
| 6,780,175 | B1 | 8/2004 | Sachdeva et al. |
| 7,037,321 | B2 | 5/2006 | Sachdeva et al. |
| 8,052,670 | B2 | 11/2011 | Sachdeva et al. |
| 8,377,037 | B2 | 2/2013 | Sachdeva et al. |
| 2002/0052627 | A1 | 5/2002 | Boylan et al. |
| 2004/0138529 | A1* | 7/2004 | Wiltshire ............ A61B 1/0055 600/144 |
| 2005/0049681 | A1* | 3/2005 | Greenhalgh ..... A61B 17/12022 623/1.15 |
| 2010/0280494 | A1* | 11/2010 | Matsuura ............ A61M 25/007 604/523 |
| 2014/0255246 | A1 | 9/2014 | Simpson et al. |
| 2015/0342877 | A1 | 12/2015 | Menachem et al. |

* cited by examiner

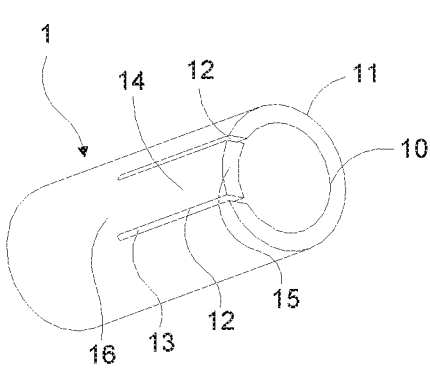
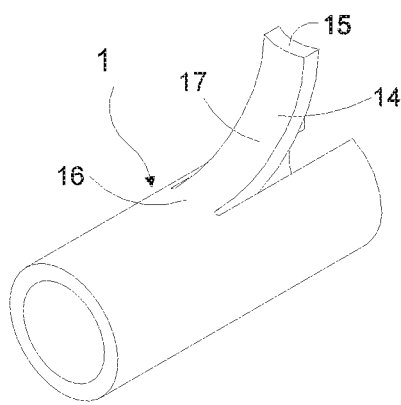
Fig. 1c
PRIOR ART
Fig. 2
PRIOR ART
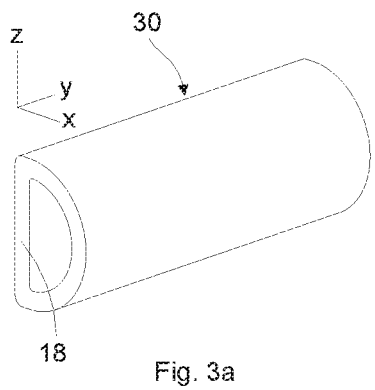
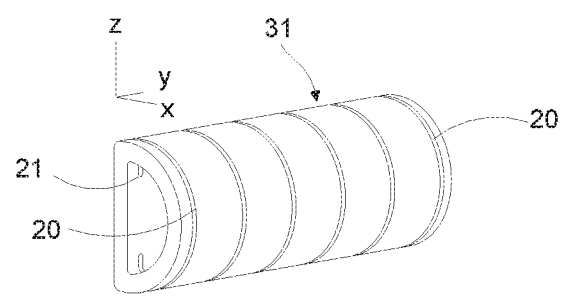
Fig. 3a
Fig. 3b
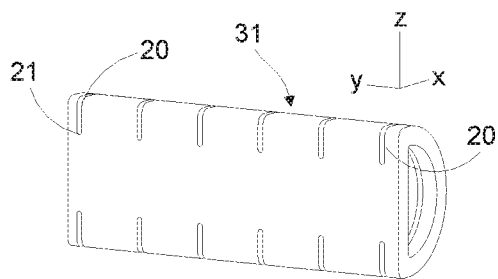
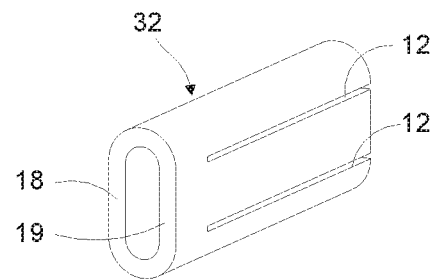
Fig. 3c
Fig. 3d
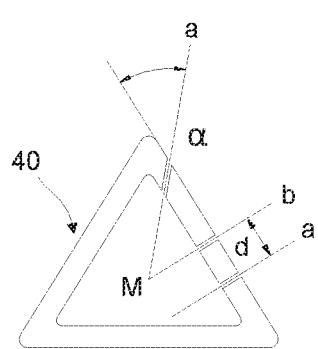
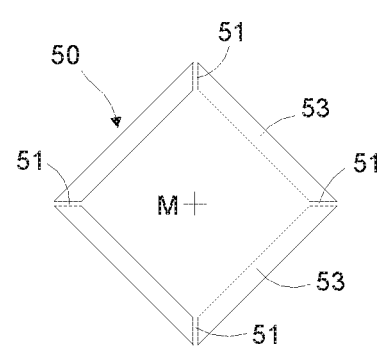
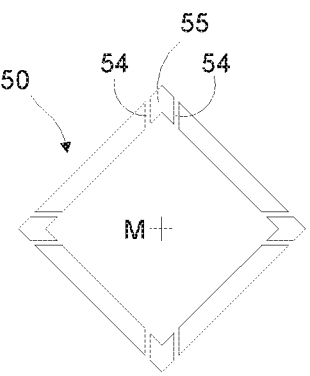
Fig. 4
Fig. 5a
Fig. 5b

TUBING FOR MANUFACTURING EXPANDABLE DEVICES

CROSS-REFERENCE TO RELATED APPLICATIONS

This application claims the benefit of U.S. Provisional Application Ser. No. 62/719,736, filed Aug. 20, 2018.

BACKGROUND

This disclosure relates generally to the field of producing improved devices from tubing, including shape memory alloys like Nitinol, and more particularly to the use of improved tubing with a non-circular cross section for the production of expandable devices.

There are numerous examples of devices that are made out of tubing with a circular cross section for outer surface as well as for the inner surface. Such devices are already described in the U.S. Pat. Nos. 5,885,258; 6,780,175; 7,037,321; 8,052,670 and 8,377,037, all by the author of the present disclosure, giving examples of embodiments of expandable devices made of Nitinol tubing.

Traditional solutions to improving the production process of round (that is to say, concentric) Nitinol tubing and to make better devices out of this tubing have included varying numerous parameters, including variations in heat treatment, plateau stresses, alloy composition and purity, amount of cold work, recovery stress, polishing and many more. Nitinol alloys with improved characteristics are described in patent publications like U.S. Pat. No. 6,428,634 by the author of the present disclosure, US 2014/0255246 by Simpson and US 2002/052627 by Boylan. Some of these alloys contain additional elements besides nickel and titanium in order to improve specific mechanical and thermomechanical properties. Optimization of the concentricity to create an even wall thickness is a major demand, in order to ensure that the material has homogenous mechanical properties. Until now the focus was always on these concentric tubes. In one conventional form, two parallel slots may be cut along the axial direction of such circular cross-section profile tubing such that an expandable tine retains an uncut section between the two slots with a concave inner surface and a convex outer surface. When such a section is bent outward in its length direction in order to start shape setting, the curved cross section of the tine can cause buckling in one place, thus causing an uneven deformation or—in extreme cases—failure. Moreover, the non-planar geometry increases the bending moment of inertia that in turn significantly reduces the flexibility of such tines relative to those with substantially planar, flat profiles.

The author of the present disclosure has determined that there is a need for tubing that has different cross sections in order to create a new unused parameter that allows the design and production of better components with properties that are related to the shape of the base tube being used. This can lead to new options, including reduction of crossing profile and improved mechanical characteristics of components. As such, the special cross-sectional geometry of the tubing enables the cutting of bendable sections that can take up larger deformations and that will have improved mechanical properties.

SUMMARY

According to an aspect of the present disclosure, an intra-corporal medical device made up of one or more tubes made of a memory metal alloy is disclosed. The tube includes an outer surface with a cross section profile with at least one substantially non-concave side plane that is flatter than that of a concave cross section of a concentric tube with similar outer and inner dimensions. The tube also includes a pattern made up of slots formed in the at least one substantially non-concave side plane such that tines are defined thereby. In this way, the tines are made being bendable without buckling in such a way that the device is capable of expansion and contraction.

According to another aspect of the present disclosure, a medical device made up of one or more tubes is disclosed. The tube includes an outer surface with a cross section profile with at least one substantially non-concave side plane that is flatter than that of a concave cross section of a concentric tube with similar outer and inner dimensions. The tube also includes slots formed in the at least one substantially non-concave side plane such that tines are defined thereby, the tines being bendable without buckling in such a way that the device is capable of expansion and contraction.

According to another aspect of the present disclosure, a method of making an intra-corporal medical device is disclosed. The method includes providing one or more tubes each of which has an outer surface with a cross section profile with at least one substantially non-concave side plane that is flatter than that of a concave cross section of a concentric tube with similar outer and inner dimensions, and cutting a plurality of slots in the flattened side plane such that tines are formed thereby. In this way, the tines are capable of bending without buckling in such a way that the device is capable of expansion and contraction.

It will be appreciated that within the context of the present disclosure that the term "cutting" includes any process to make tubing with a specific pattern of tines by cutting, etching, grinding or any other method. In one particular form, such cutting is achieved through laser cutting.

After the cutting and cleaning the device is shaped into the desired shape, in case of shape memory alloys followed by cold work, mostly combined with a heat treatment with a mechanical means holding all tines and the base tube constrained in or on a mandrel or fixture in the proper geometry. This is called "shape setting".

The base tube according to the disclosure has at least one flat plane, but can have many shapes. Even a plane that is not perfectly flat, but with less curvature in its cross section than a circular tube with comparable dimensions would have, will already lead to improved characteristics for the tine that is cut out of such a less curved plane. Sometimes the outer planes may be perfectly flat, while the inside of the tube still has more or less curved "planes". The opposite may also be the case, with perfect flat inner planes but curved outer "planes". Such embodiments are meant to be part of the claimed disclosure as well. The elastic energy stored in devices according to this disclosure is potentially much higher than for devices with the same outer dimensions that are made of conventional concentric tubing. This also opens new ways to manufacture components with smaller profile, still having the same radial strength as devices made from conventional tubing.

Examples of embodiments are a flattened tube with a partly round and partly straight cross section, a triangular tube, a square or rectangular tube, any polygon shape and so on. Hexagonal tubing may be cut with overlapping slots in intermittent planes from two sides to create more complex expandable devices.

As the expandable tines can be cut out in one or more flat planes, the cross section of the tines show inner and outer surfaces that both are flat and parallel. This makes them easily shapeable without the risk of buckling or breaking, like the tines that are made out of circular tubing. The problem with tines cut in circular tubing is that their cross section may suddenly be deformed from curved into flat, where the material at the original concave inner tube surface undergoes excessive and uneven deformation when it becomes the outer convex surface of a bent tine. Off course the same problem counts for tines that are bent inward instead of outward.

The direction of the slots may be parallel to the main axis, like in the following examples and drawings, but it can also be made in other directions, with a curved pattern and various angles with the main axis. The width of the tines may vary over its length and they may also be made in more than one plane of the tube wall. This means that one tine can run over at least two of the flat planes, causing a kind of angled connection at the junction between the two planes.

If the expansion force of the tines is too low to withhold a certain load that tends to pull out an anchor, a plug can be pulled against the expanded tines to lock them in their expanded state. Collapse of the tines is then made impossible.

For some applications the tines may be used as an unidirectional or multidirectional releasable lock.

It will be appreciated by those skilled in the art having regard to this disclosure that other modifications of this disclosure beyond these embodiments specifically described here may be made without departing from the spirit of the disclosure. Accordingly, such modifications are considered within the scope of the disclosure as limited solely by the appended claims.

Improved products can be made by starting with special shaped tubing which has a cross section existing of a number of flat planes that are connected in tangential direction to form an oblong tubular shape. A pattern of slots that is made in the tubular surface divides the base tube in a part that stays in its original tubular form and a plurality of more flexible parts that will be defined here as "tines" for the purpose of this description. These tines are the parts that are supposed to make a movement out of the plane where they were originally located in the uncut tube surface. This movement can be of any kind, dependent of the type of application. Normally the tines stay connected to the base tube, at least on one end, but possibly also on more than one end or even to one or both ends plus eventually one or more connection point between the ends. This is for example the case in all kinds of stents, filter frames and valve frames, where the tines are mostly defined as struts, beams or other terms.

BRIEF DESCRIPTION OF THE DRAWINGS

The following detailed description of the preferred embodiments of the present disclosure can be best understood when read in conjunction with the following drawings, where like structure is indicated with like reference numerals and in which the various components of the drawings are not necessarily illustrated to scale:

FIG. 1*c* shows a conventional round tube with circular cross section for inner and outer surface, provided with a pair of slots;

FIG. 2 shows the tube of FIG. 1*c* after having bent the tine outward;

FIG. 3*a* shows a tube according to the disclosure with one flat side plane connected to a cylindrical main section;

FIG. 3*b* shows the tube of FIG. 3*a*, with a series of slots only in the wall of the cylindrical main section;

FIG. 3*c* shows the rear side of the tube of FIG. 3*b*;

FIG. 3*d* gives a tube with two flat planes connected to two rounded sections and a pair of slots in the flat section;

FIG. 4 shows a triangular tube with a centre M and three types of slots in the wall;

FIGS. 5*a* and 5*b* give two examples of a square tube with slots in the four corners;

DETAILED DESCRIPTION

The advantages of the disclosure will become more apparent after reference to the following description, wherein some embodiments are elucidated. Any product made of shaped tubing with tines cut in flat tubing sections are meant to be included in the embodiments according to the disclosure. In one form, shape memory materials are used in the formation of various devices as disclosed herein, including medical devices in particular and more particularly intra-corporal medical devices. The properties of such shape memory alloys include shape memory effect, linear and non-linear pseudoelasticity (also referred to as superelasticity) and strain hardened cold working, all of which may be used in numerous flexible, steerable and expandable devices including but not limited to catheters, connectors, anchors, grippers, retrieval devices for particles, baskets, filter baskets, filters, vascular closure devices, stents, reamers, cutting devices, valve frames, miniature septal occlusion devices, electrode anchors, needles, bone anchors, closure plugs, left atrial appendage closure devices and locking devices.

In one form, medical devices formed from the final products are inserted into a patient with some internal or external restraining means that holds the tines in a deformed state, and the tines will take their desired shape as soon as they are delivered from this restraining means. Other products may respond to temperature changes, causing the shape memory effect.

The external restraining means, also called a delivery tube, may be a rigid tube, eventually with a sharpened distal end, working as an insertion needle that can cut a hole in all kinds of soft or harder tissue. In other devices the delivery tube may have a flexible or even steerable distal end that allows placement of the device under an angle with the main length axis of the system. Such flexibility can be achieved by all known methods, including but not limited to coiling, braiding, cutting of slots in the wall and many more options.

The delivery tube may be a flexible and eventually steerable catheter as well, and it may be provided with an optical system for imaging purposes or a laser system for drilling, cutting or ablation purposes.

The following description of the drawings gives some options for devices that are manufactured from tubing with at least one more or less flat plane that enables shape setting of tines or struts that have a cross section which is neither concave nor convex. In the disclosure the word "diameter" is used also for all kinds of polygon shapes and other examples, although it should be read as the outer dimension of the cross section, as if it was a round tube with similar outer dimension.

Figure 1A:
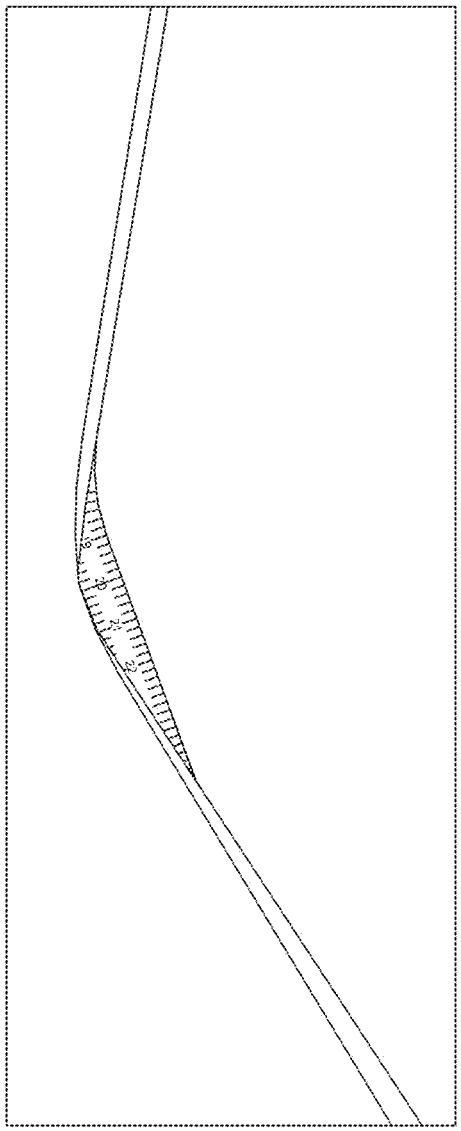
FIG. 1*a* shows a conventional tape measure with a curved cross section when it is bent towards the concave side.
Figure 1B:
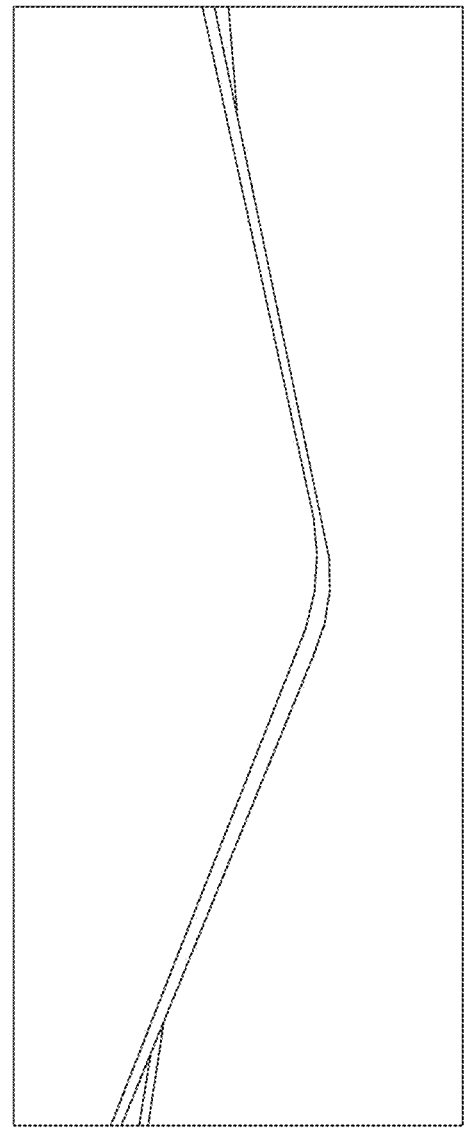
FIG. 1*b* shows the tape measure of FIG. 1*a* when it is bent towards the convex side.

Referring first to FIGS. 1a and 1b and by way of reference, a conventional tape measure made of a strip of metal with a curved cross section is shown bent into the concave and convex direction respectively. As can be seen, it is not possible to create a smooth and even bend in such a piece of strip without the risk of buckling and excessive local deformation. The problem is merely the curvature of the strips cross section, and the larger the angle of this curvature is, the larger the problem. If the width of the strip is only describing a curvature angle of a few degrees, then the bending may be still smooth.

Referring next to FIG. 1c, a conventional round tube 1 is shown with circular cross section for inner surface 10 and outer surface 11, provided with a pair of slots 12, ending in points 13. These slots form a tine 14 with a curved cross section 15, which is still connected to the tube 1 at base 16.

FIG. 2 shows the tube 1 of FIG. 1c after having bent the tine 14 outward. Somewhere the tine 14 may get the same buckling deformation as that which can be envisioned by looking at the cross-sectional view of the measuring tape as depicted in FIGS. 1a and 1b, for example at location 17 or at the base 16. When products are manufactured from round tubing, it is always a challenge to prevent this plastic deformation by buckling. One solution is keeping the width of the tine as small as possible, thus having a curvature of only a few degrees. Then the shape setting may not be a problem, but when the curvature is stronger, for example if the tangential angle of the tine is relatively large or the wall thickness is large, buckling may occur.

FIG. 3a shows a tube 30 according to the disclosure with one flat side plane 18 connected to a cylindrical main section. Such a tube will allow the manufacturers to make a much wider and stronger tine, that does not suffer the described problems. This opens new ways for designers of numerous types of products. Many variants of tube geometries with flat planes are possible.

Using a tine with parallel planes also enables the increase of the wall thickness, without the risk of buckling during bending and/or shape setting. Therefore much stronger devices can be made, keeping the outer dimensions of the tube as small as possible. This finally will lead to products with a smaller delivery profile or stronger devices with the same profile as devices made of conventional round tube.

FIG. 3b shows the long tubular component 31 of FIG. 3a, that now has one preferential bending plane. This can be achieved by making a series of parallel slots 20 perpendicular to the length axis, where the slots run into the flat plane 18 until end points 21. The hinges that remain uncut in flat plane 18 will make the tube very flexible, while there is no excessive deformation upon bending around axis Z, because the cross section of each hinge is pure rectangular. However, bending around axis X or Y is almost completely prevented by the hinge shape. Such tubular devices can be used in all kinds of catheters, for example in mitral valve treatment or transcatheter aortic valve implantation (TAVI) procedures, where oriented flexibility in only one bending plane is required. Bending of such rectangular hinges also causes less fatigue problems because there are no stress concentrations like in convex hinges.

FIG. 3c shows another view on the rear side of the device 31 of FIG. 3b.

FIG. 3d gives an example of a tube 32 with two flat planes 18 and 19, connected to two rounded sections and a pair of slots 12 in the flat sections. The two flat planes on both sides of the tubing may be parallel, but may also be placed under any angle with each other.

FIG. 4 shows a triangular tube 40 with a centre M and three types of slots a, b and c in the wall. Slot a is cut in the direction towards point M, but with an angle α with the flat plane. Slot b is perpendicular to the flat plane and directed towards centre M. Slot c is perpendicular and cut with an offset d from centre M. Combination of slot a with slot b or c would result in a tine that has a cross section of a trapezium, with an inner surface that is less wide than the outer surface. All kinds of variations can be made, but in all cases the two surfaces of the tine will be flat, resulting in an and easily shapeable tine.

FIG. 5a gives a square tube 50 with slots 51 in the four corners and four tines with cross section 53, each having the shape of a trapezium. The entire tube surface is transformed in tines in this example, but if slots 54 would be cut like in FIG. 5b, with some tube struts 55 left on the corners, the base tube remains connected by struts 55 with sections on different axial locations.

These slots 54 may be oriented towards the centre M of the tube, or have any offset with this radial orientation, like shown here.

Figure 6A:
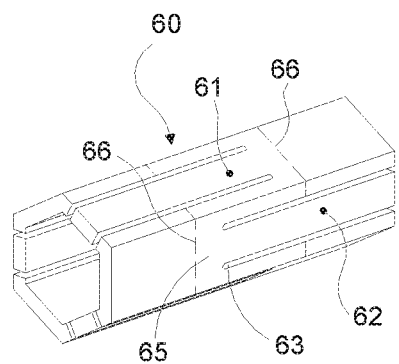
FIG. 6*a* shows a tube with hexagonal cross sections and two sets of overlapping slots, resulting in tines with connection points close to the middle section of the tube.

FIG. 6a shows a tube 60 with hexagonal cross sections and two sets of slots, resulting in overlapping sets of tines 61 and 62, with connection points close to the middle section of the tube. From the left end three tines 61 are formed in the first, third and fifth plane, while from the right end tines 64 are formed in the second, fourth and sixth plane, counting around the tube surface. The slots forming tines 61 end at base 63, while the slots forming tines 64 end at base 65. Dependent on the application the axial overlap of the tines may be varied or there may be no overlap at all. The dashed lines in FIG. 6*a* show how the remaining ends of the original tube may be cut away at a location depicted as dashed lines 66 near the bases 63 and 65 of the tines in order to make the whole device shorter, at least in its expanded state.

Optionally the tines 61 of FIG. 6*a* do not run entirely until the tube ends, thus leaving uncut sections of the original tube on one or both ends, for example for attachment purposes of sutures or anything else.

Figure 6B:
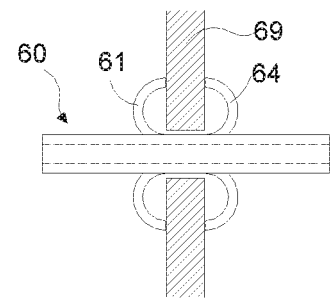
FIG. 6*b* gives the tube of FIG. 6*a* after shape setting, creating a double umbrella structure.

FIG. 6*b* gives the tube 60 of FIG. 6*a* after shape setting, creating a double umbrella structure, which may be used to clamp some tissue 69 in between, for closure or attachment purposes. Closure may be achieved by attaching a polymer membrane to the expandable sections and inside the inner lumen of the tube. If the device of FIG. 6*a* is used for attachment purposes, a body part or a wire, catheter, electrode or any other device remains attached to the expandable tubular part, for example by connection to an eyelet in the tube wall.

Figure 7A:
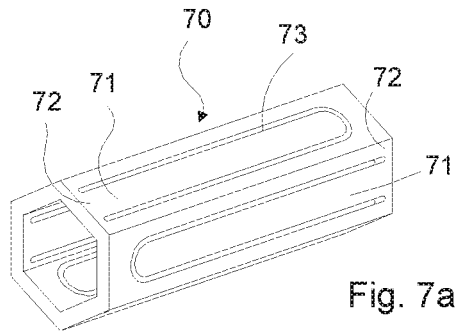
FIG. 7*a* shows a tube slightly different from the one in FIGS. 6*a* and 6*b*, now also with overlapping slots, but with tines that have their connection points further apart from each other.

FIG. 7*a* shows a tube 70 slightly different from the one in FIGS. 6*a* and 6*b*, now also with overlapping slots, but with tines that have their connection points 71 further apart from each other. In this example the tube ends 72 cannot be removed, contrary to the example of FIGS. 6*a* and 6*b*, because the tines would fall out of the tube then.

Figure 7B:
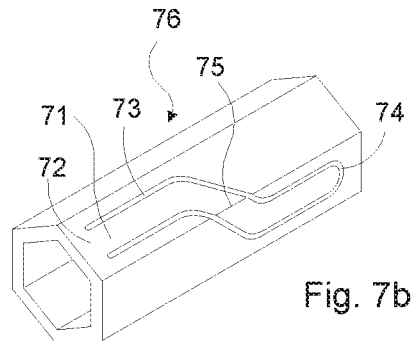
FIG. 7*b* shows a hexagonal tube, with a tine that runs over two adjacent flat planes.

FIG. 7*b* shows a device 76 with slot 73, resulting in a tine 71 that runs over two adjacent flat planes, starting at its base 71 in the first plane and running until its free end 74 in the second plane. This results in a tine, made of two flat planes, connected at a sharp angled connection point 75. In other embodiments the tine may run over more than two planes or over one flat plane and a curved plane, in an embodiment like the examples of FIGS. 3*a* through 3*d*. Slots may be cut in several planes and in all kinds of directions, with all possible angles with the main axis of the tube.

Such devices, with tines that have multiple orientations and that run over several planes, may be used for catheters, stents, valve frames, reamers, baskets, filter frames and many more.

Figure 8A:
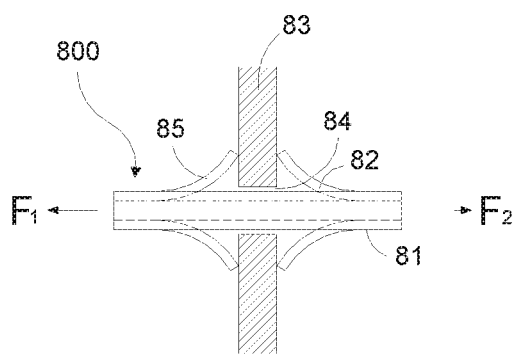
FIG. 8*a* gives a schematic side view of the device of claim 7a after shape setting and mounted through a hole in a tissue, gripping it from both sides.

FIG. 8*a* gives a schematic side view of device 800 made of tube 81 similar to FIG. 7*a* after shape setting the tines 82 and mounted through a hole 84 in a tissue 83, gripping it from both sides after expansion of the opposing tines 85. Such devices may be combined with some other material of any kind, including several layers, eventually of different materials, including metals, polymers, fabrics or organic tissues. A polymer plug or membrane may be attached or covering the tines 82 and/or 85 to ensure that there is no leakage through the remaining gap in hole 84. Hole 84 can be a septal defect in the heart, for example, which has to be closed and sealed.

Such a device can withstand high pulling forces F1 and F2 in both directions, without the risk that the tines will bend to their unexpanded state and loose their grip.

Figure 8B:
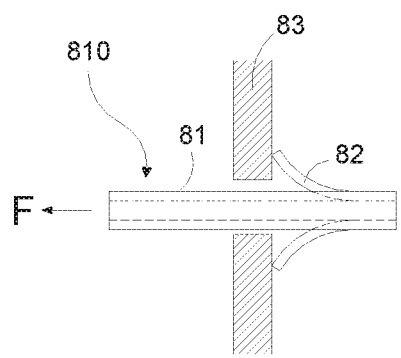
FIG. 8*b* shows a device that is put through a hole with reverse tines that hold on one side of the tissue.

FIG. 8*b* shows a device with tube 810 that is put through a hole with reverse tines 82 that only hold on one side of the tissue, able to withstand axial forces F in one direction. Pulling out in the direction of force F is almost impossible.

Figure 8C:
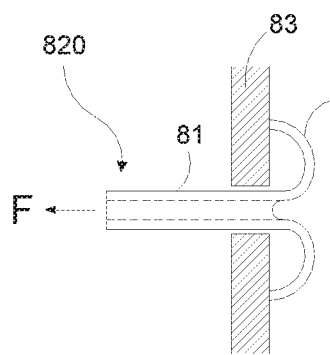
FIG. 8*c* gives another device that holds on one side of the tissue with tines that can be pulled out again with extra force.

FIG. 8*c* gives another device 820 with tines 86 that can be pulled out again, if force F is sufficient to bend tines 86 back into their straight shape. Repositioning with almost zero force can also be achieved by pushing the delivery tube or a separate retrieval tube over the tines in order to collapse them to a state where the diameter is equal to the original tube size.

Figure 8D:
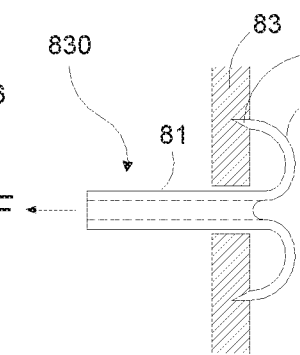
FIG. 8*d* shows a device with sharpened tines that cut themselves through the tissue.

FIG. 8*d* shows a device 830 with tines 86, having sharpened points 87 that cut themselves through the tissue 83 for better anchoring purposes.

Figure 8E:
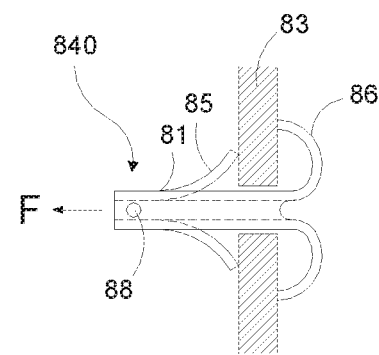
FIG. 8*e* shows the device of FIG. 8*c*, now with additional tines on the opposing side of the tissue layer.

FIG. 8*e* shows device 840, as combination of devices as shown in FIGS. 8*b* and 8*c*, with tines 86 on one side and additional tines 85 on the opposing side of the tissue layer for fixation in both directions. Eventually a separate suture wire can be attached to a drilled eyelet 88 in the tube wall.

Figure 8F:
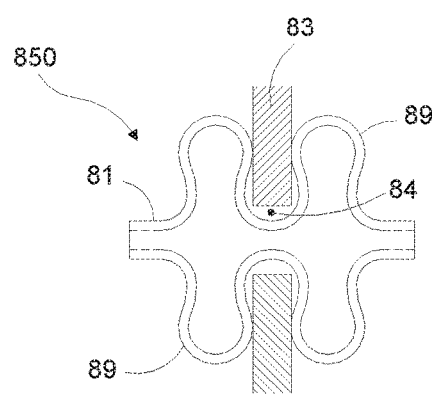
FIG. 8*f* gives a device with two sets of tines that each take a bulbous shape after delivery.

FIG. 8*f* gives a device 850 with tube 81, including two sets of tines 89 that each take a bulbous shape after delivery. The number of tines on both sides can be chosen, and the tines may run over more than one plane, like the one shown in FIG. 7*b*. Several tines per flat plane can be used as well. Both bulbous sections may expand far enough to become almost flat by contraction in length direction, resulting in two umbrella-like structures that can close a relatively large hole 84 in tissue 83. An additional covering of the bulbous structures can ensure complete closure to prevent leakage. The covering may be a polymer mesh or membrane that surrounds the bulbous structure, or the struts may surround the covering. One example is a closure device for septal defects in the heart. Another example is the use as a suture anchor for attachment to a valve leaflet.

Figure 8G:
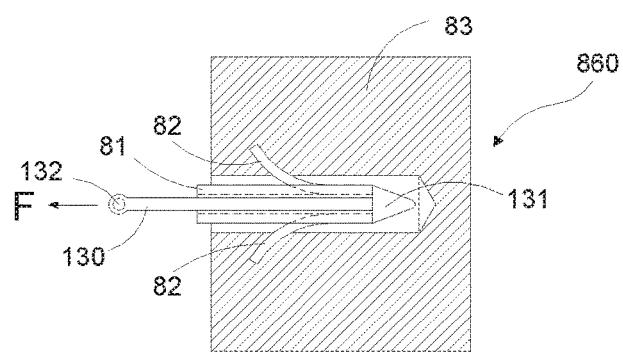
FIG. 8*g* shows a device that is put into a blind hole, with reverse tines that anchor themselves into the tissue.

FIG. 8*g* shows a device 860 with tube 81 that is put into a blind hole with reverse tines 82 that hold firmly inside of the tissue 83, able to withstand axial forces F in one direction. Pulling out in the direction of force F is almost impossible. Such a blind hole may be a drilled hole in bone or an intramedullary canal or a hole in soft tissue. The latter may be made by insertion the device with a delivery tube that has a sharpened distal end. Such devices can be used as endosseous dental implants, bone anchor pins, or anchors in softer tissue like muscles, including the wall of the heart.

Figure 8H:
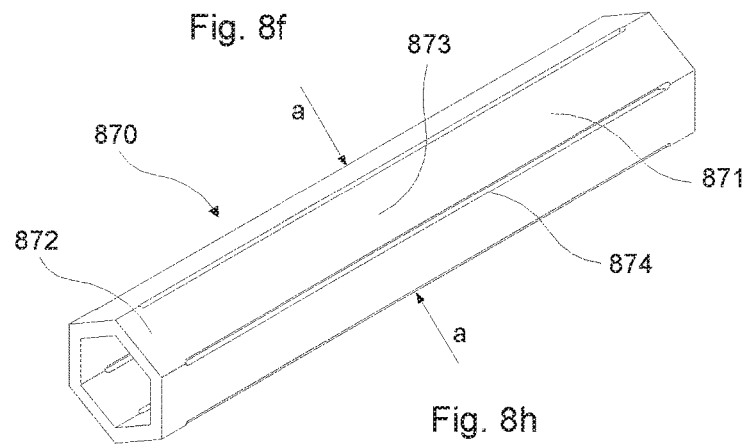
FIG. 8*h* shows a monolithic tubular basket with six tines, each with rectangular or trapezoidal cross section, which can be used as an expandable frame for filters or as a retrieval basket to capture particles.

FIG. 8*h* shows an example of an expandable basket 870 with six tines 871 with an almost rectangular cross section, which ensures enlarged stability in tangential direction, while radial expansion of the centre sections 873 near the middle depicted as a-a is relatively flexible. Such a basket may be of the self-expanding type or it may be self-collapsing. If it is self-expanding, it will be held on its smallest diameter by a delivery tube. If it is self-collapsing, it will be expanded by decreasing the axial length by means of a separate wire that pulls the proximal and distal ends closer to each other. The rectangular (or trapezoidal) cross section prevents buckling in tangential direction and makes such a basket very stable in every state of expansion. Baskets can be used in stone or tissue retrieval devices, pump frames, embolic protection frames, valve frames, and many more. The expandable tines may be combined with a surrounding flexible membrane, or the membrane is attached to the inner surface of the tines. If needed, the slot width 874 can be varied over the length of the tines 871 in order to give them preferential bending spots (not shown here). In this embodiment both tube ends 872 remain uncut, but one of the ends may be slotted as well. Then the structure is open on one side.

Figure 8I:
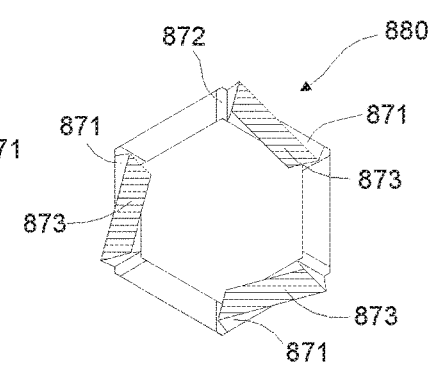
FIG. 8*i* gives a cross section of the basket similar to the one depicted in FIG. 8*h*, but now the central sections of three tines are rotated over their length axis over an angle of 10 degrees in order to become stronger in radial direction, also resulting in a reaming effect by rotating the device with its slightly rotated sharpened tines in counter-clockwise direction.

FIG. 8*i* shows a cross section 880 of the middle part depicted as a-a of the basket 870 with six tines 871 of FIG. 8*h*.

Three of the tines 871 have been rotated to position 873 by applying torque to each tine in order to change the tangential orientation of the trapezoidal cross section into a slightly more radial orientation. Such a device can be used as an expandable reamer with 3 angled tines with sharpened edges on one side of the struts. Rotation in clockwise direction will not cause cutting, but in the opposite direction the sharp edges will start cutting. Adjusting the diameter can either be achieved by moving the expandable reamer more or less out of a surrounding delivery catheter, or by causing expansion by changing the length of the device by axial force.

If the torque angle is larger, for example 90 degrees in the middle, this rotation causes a huge increase in radial force, because the bending stiffness of the trapezoidal (or eventually rectangular) cross section relates to its height with the second magnitude. Such devices can be used when extra strength is required. If the edges are sharpened such a device can also be used for reaming purposes, like the struts in a scoring balloon that is used to break up calcified plaque in arteries. The torque angle between the original plane in the tube wall and the final angle of the tine with this original tangential plane after the torsion is completed can have any value between 0 and 90 degrees, dependent on the application.

Figure 9A:
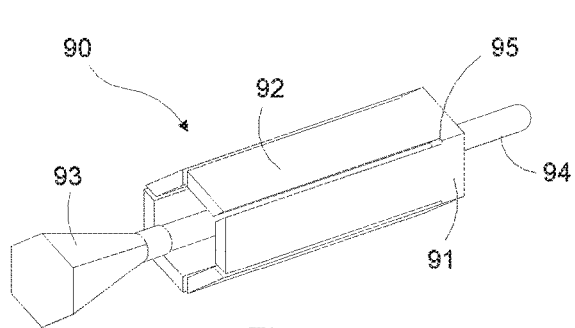
FIG. 9*a* shows a device with expanded tines and a plug that can be pulled into the tubular device to lock the tines in their expanded state, by preventing the collapse of the tines.
Figure 9B:
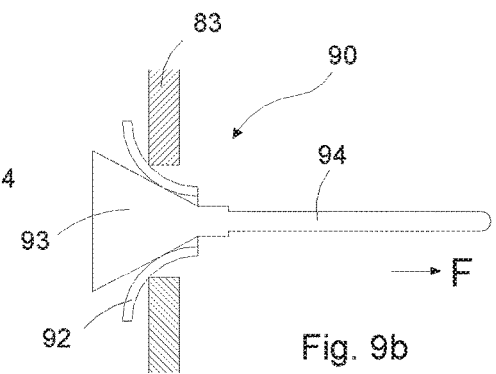
FIG. 9*b* gives the device of FIG. 9*a* after locking.

FIG. 9a shows a device 90 made of tube 91 with expandable tines 92 and a tapered plug 93 that can lock the tines in their expanded state, by preventing the collapse of the tines. The outer dimensions of the largest end of plug 93 and tube 91 can be equal or slightly different. Plug 93 may have a flat (as drawn), rounded or sharpened distal tip. As soon as the expansion of tines 92 is complete the plug 93 may be pulled into tube 91 by means of puller 94 in order to engage the plug with the base 95 of the tines 92. Puller 94 may be attached to a suture, or directly to another device or body part. After locking the tines cannot return to their unexpanded state and a strong anchoring is achieved. This is shown schematically in FIG. 9b in a cross section.

Figure 10:
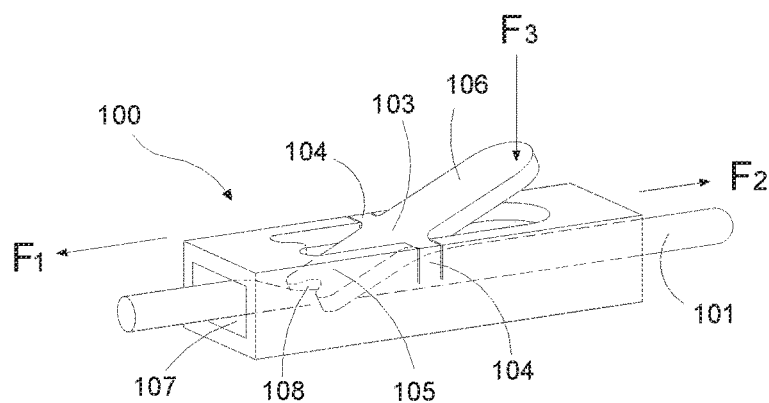
FIG. 10 shows a releasable unidirectional locking device with a movable tine, which can be used for internal or external locking purposes.

FIG. 10 gives a tubular device 100 with a special locking function, similar to well-known tie wraps. A wire or suture 101 can easily be pulled through the tube in one direction with force F1, but if force F2 is applied in the other direction an inward bending tine 103 will be pulled into a more inward bending state by the friction of the moving wire and the tine will finally completely lock the wire against the inner surface of the tube. Release of the lock is possible by bending tine back to its original position. As can be seen, a single tine 103 is cut in a tube wall. The tine has two hinge points 104 and two elongated sections 105 and 106. By shape setting the tine is programmed to bend inward with section 105, and the opposing section 106 will then bend outward. The inward section 105 almost engages the opposing inner wall 107 of the tube, and the gap 108 between tine end and wall 107 is smaller than the dimensions of the wire 101 that runs through the tube. In one direction the wire 101 can easily be pulled through device 100, but in the opposing direction the tine 103 will push the wire firmly against the opposing wall 107 and prevents any further movement in the direction of F2. The locking force of the suture wire can be enlarged by providing it with a series of knots along its length. Release is possible by pushing opposing section 106 down, thus lifting section 105 because of hinges 104. Such a device can by delivered with an outer tubular catheter or introducer that holds sections 105 and 106 of tine 103 in their constrained flat position. The wire can then be moved in both directions. As soon as the outer tube is pulled away the unidirectional lock starts functioning, similar to a well-known tie-wrap.

The releasable lock can also be used as an anchor (such as the one depicted in FIG. 8g) that holds on the outside, after it is put into a hole. Then the anchoring comes from outward bending section 106, which holds itself locked by engagement with the wall of the surrounding hole. Section 106 can be released by pushing a retainer pin into the right-side end of tube 100, which lifts section 105 towards the upper tube wall, causing section 106 to move out of its anchoring position. Such a device may be used as a bone anchor with zero insertion force, which opens up into its anchoring position as soon as the retainer pin is pulled out of the tube. If repositioning or removal of the anchor is required, the pin can be pushed into the tube and the anchoring section will rotate back to its neutral position. A suture wire can connect such a bone anchor to other parts of the body.

It is an object of the present disclosure that devices are made out of tubing having at least one substantially flat plane with parallel outer and inner surfaces.

It is also an object of the present disclosure that the cross section of the tubing has the shape of a polygon.

Another object of the present disclosure is that tines are cut out of the tubing wall and that these tines are cold worked and/or shape set in order to give them a shape that is different from the original shape after the cutting process.

It is also an object of the present disclosure that tines may bend outward from the tubing wall into an expanded state or bend inward towards the centre of the tube.

Another object of the present disclosure is that devices are delivered into a constrained state with minimal delivery profile inside a surrounding delivery tool and then released from the delivery tool in order to allow them to change into the programmed geometry.

Still another object of the present disclosure is that devices are held in their constrained insertion state with minimal delivery profile by means of an internal biasing pin, which can be removed in order to cause the change into the programmed geometry.

In another object of the present disclosure is devices stay in their unbiased insertion state with minimal delivery profile, while an external force is used to bias the devices into a different configuration with dimensions that differ from their insertion state.

Another object of the present disclosure is that devices have a releasable locking function with at least one tine that prevents the movement of a suture through the device when the tine is in its programmed position. The locking position of that tine may be changed into an unlocking position by an external or internal biasing tool.

It is further another object of the present disclosure that the tubing has at least one plane that is not perfectly flat, but that has a curvature of the cross section that is less than it would be in a tubing of same outer size, but with only a circular cross section.

Another object of the present disclosure is that the tubing is made of a polymer, ceramic, composite, metal and combinations thereof.

It is further another object of the present disclosure that the tubing is made of any shape memory alloy with properties including shape memory effect, linear or non-linear pseudoelasticity (also defined as superelasticity), or the tubing is just a strain hardened cold worked shape memory alloy, like Nitinol. Moreover, using Nitinol may include a process of cutting, etching, grinding or the like in order to cut a specific slot pattern in the wall, followed by a treatment (such as heat treatment) of shaping the device to its final form, such as by shape setting, as well as by alternative techniques for shaping that employs strain hardening or cold work.

Still another object of the present disclosure is that devices made of the present improved tubing comprise expandable, collapsible, lockable and release-able devices including but not limited to connectors, anchors, grippers, retrieval devices for particles, pump frames, baskets, filter baskets, filters, vascular closure devices, stents, reamers, cutting devices, valve frames, miniature septal occlusion devices, electrode anchors, bone anchors, intramedullary pins, blind plugs, closure plugs, tissue plugs, left atrial appendage closure devices, locking devices, adjustable locking devices, releasable locking devices and many more.

It is also an object of the present disclosure that tines with more or less parallel inner and outer surface can be bent further and easier without permanent plastic deformation than tines of the same wall thickness, having a curved cross section.

Each endoluminal device made of tubing substantially as described in the present application is considered as an object of the present disclosure.

Each endoluminal device using one or more of the novel features as described in the present application is considered as an object of the present disclosure.

The method of making an endoluminal device of tubing substantially as described in the present application is considered as an object of the present disclosure.

The method of using an endoluminal device of tubing substantially as described in the present application is considered as an object of the present disclosure.

Although in this present disclosure only the application of a number of devices made out of tubing with at least one flat plane were mentioned, it is an object of the present disclosure that any other embodiment, using the same type of tubing, can be used.

It is within the scope of the present disclosure that any material or any combination of materials can be used in any configuration to make such devices.

It is noted that terms like "preferably", "generally" and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure. Likewise, for the purposes of describing and defining the present disclosure, it is noted that the terms "substantially" and "approximately" and their variants are utilized herein to represent the inherent degree of uncertainty that may be attributed to any quantitative comparison, value, measurement or other representation, as well as to represent the degree by which a quantitative representation may vary without resulting in a change in the basic function of the subject matter at issue.

While certain representative embodiments and details have been shown for purposes of illustrating the present disclosure, it will be apparent to those skilled in the art that various changes may be made without departing from the scope of the disclosure, which is defined in the appended claims.

The invention claimed is:

1. An intra-corporal medical device comprising at least one tube made of a memory metal alloy programmed for an effect selected from a group of effects consisting of shape memory effect, linear pseudoelasticity, non-linear pseudoelasticity and elasticity by strain hardened cold work, the at least one tube comprising:
    an outer surface defining a cross sectional shape with at least one side plane, which is flatter than that of a concave cross section of a concentric tube with corresponding outer and inner dimensions; and
    a pattern of a plurality of slots cut in the at least one side plane of the at least one tube such that a part of the at least one tube is divided from at least one tine that is formed of the at least one side plane of the at least one tube, the at least one tine being bendable without buckling in such a way that the intra-corporal medical device is capable of bending, expansion and contraction, wherein the part of the at least one tube stays in its original form.

2. The intra-corporal medical device of claim 1 where the inner and outer surfaces of the cross section of the at least one tine are perfectly parallel and flat.

3. The intra-corporal medical device of claim 1 where the inner surface of the cross section of the at least one tine is flat and the outer surface only slightly curved.

4. The intra-corporal medical device of claim 1 where the outer surface of the cross section of the at least one tine is flat and the inner surface only slightly curved.

5. The intra-corporal medical device of claim 1 wherein at least a portion of the alloy is made of Nitinol.

6. The intra-corporal medical device of claim 1, wherein it is held in a constrained state inside a surrounding delivery tool during insertion into a body part and wherein the intra-corporal medical device expands to its programmed state when it is pushed out of the delivery tool.

7. The intra-corporal medical device of claim 1, wherein it is inserted into a body part in an unconstrained unexpanded state and wherein the intra-corporal medical device is expanded to its final reconfigured state by means of an external axial force.

8. The intra-corporal medical device of claim 1, wherein the at least one tube has several flat side planes in which such tines are cut out.

9. The intra-corporal medical device of claim 8, wherein the cross section of the at least one tube forms a polygon with at least 3 flat planes.

10. The intra-corporal medical device of claim 1, wherein the at least one tine when bent forms a basket structure, comprising an elastic polymer surrounding or surrounded by the device.

11. The intra-corporal medical device of claim 1, wherein the at least one tine forms an anchoring section for attachment inside or to body tissue, including but not limited to muscles, heart wall, skin, membranes, valve leaflets and bone parts.

12. The intra-corporal medical device of claim 1, including a releasable lock with a hinged tine that holds on an inserted suture wire, wherein the lock is opened out of its locking position by pushing an opposing part of the hinged tine into its original as-cut position by sliding a delivery tool over the at least one tube.

13. The intra-corporal medical device of claim 1, including a releasable lock with a hinged tine that anchors itself inside a lumen, wherein the lock is opened out of its locking position by pushing an opposing part of the hinged tine into its original as-cut position by sliding an internal biasing pin into the at least one tube.

14. The intra-corporal medical device of claim 1, wherein the at least one tine has a cross section which is rectangular or trapezoidal.

15. The intra-corporal medical device of claim 1, wherein at least a part of the at least one tine has been rotated out of the tangential plane.

16. The intra-corporal medical device of claim 15, wherein the at least one tine has a sharpened edge for cutting or reaming purposes.

17. The intra-corporal medical device of claim 1, used as an expandable anchor with outward bending tines, which are locked in their expanded position by an internal plug that prevents the return of the tines into their unexpanded position.

18. The intra-corporal medical device of claim 1, wherein the at least one tine is treated to bend inward instead of outward.

19. A medical device comprising at least one tube having an outer surface with a cross sectional shape with the at least one side plane, which is flatter than that of a concave cross section of a concentric tube with corresponding outer and inner dimensions, the at least one tube comprising a plurality of slots cut in the at least one side plane of the at least one tube such that a part of the at least one tube is divided from at least one tine that is formed of the at least one side plane of the at least one tube, the at least one tine is bendable without buckling in such a way that the medical device is capable of bending, expansion and contraction, wherein the part of the at least one tube stays in its original form.

20. A method of making an intra-corporal medical device, the method comprising:

providing at least one tube having an outer surface with a cross sectional shape with at least one side plane, which is flatter than that of a concave cross section of a concentric tube with corresponding outer and inner dimensions; and cutting a plurality of slots in the flattened side plane of the at least one tube such that a part of the at least one tube is divided from at least one tine that is formed of the flattened side plane of the at least one tube, the at least one tine is capable of bending without buckling in such a way that the intra-corporal medical device is capable of bending, expansion and contraction, wherein the part of the at least one tube stays in its original form.

21. The method of claim 20, wherein the plurality of slots define a repeating pattern.

22. The method of claim 20, wherein the at least one tube is made from a shape memory alloy.

23. An intra-corporal medical device manufactured according to the method of claim 20.

* * * * *